(12) United States Patent
Ito

(10) Patent No.: US 6,335,431 B2
(45) Date of Patent: Jan. 1, 2002

(54) METHOD FOR SEPARATION OF ISOMERS OF AZO COMPOUNDS

(75) Inventor: Toshiyasu Ito, Saitama (JP)

(73) Assignee: Wako Pure Chemical Industries, Ltd., Osaka (JP)

(*) Notice: Subject to any disclaimer, the term of this patent is extended or adjusted under 35 U.S.C. 154(b) by 0 days.

(21) Appl. No.: 09/756,652

(22) Filed: Jan. 10, 2001

(30) Foreign Application Priority Data

Feb. 15, 2000 (JP) .................................... 12-036412

(51) Int. Cl.[7] .............................. C07C 245/04; C08K 5/23
(52) U.S. Cl. .......................... 534/838; 534/887; 526/219; 526/341
(58) Field of Search ..................... 534/887, 838; 526/219, 341

(56) References Cited

U.S. PATENT DOCUMENTS 2,586,995 A    2/1952   Robertson ..................... 534/838
4,826,959 A *  5/1989   Tanaka et al. ................. 534/838

OTHER PUBLICATIONS

G. Palma et al., Chim. Ind., 52(11), p.1116–1120, 1970.
D. Lim, Collection Czechoslov. Chem. Commun. vol.33, p. 112–113, 1968.

Yasuyuki Kita et al.: "Practical Radical Additions under Mild Conditions Using 2,2'-Azobis (2,4-dimethyl-4-methoxyvaleroni trile) 'V–70! as an Initiator," Organic Process Research & Development, vol. 2, No. 4, 1998, pp. 250–254.

* cited by examiner

Primary Examiner—Fiona T. Powers
(74) Attorney, Agent, or Firm—Armstrong, Westerman, Hattori, McLeland & Naughton, LLP

(57) ABSTRACT

A method of separation of a racemic isomer and a meso isomer from a mixture of a racemic isomer and a meso isomer of a compound shown by the general formula [1]

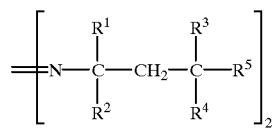

[1]

(wherein $R^1$ and $R^2$ are each independently a lower alkyl group or a cyano group, which are different from each other, $R^3$ and $R^4$ are each independently a lower alkyl group, and $R^5$ is a hydrogen atom or a lower alkoxy group), which comprises treating the mixture with a water soluble organic solvent.

23 Claims, No Drawings

METHOD FOR SEPARATION OF ISOMERS OF AZO COMPOUNDS

BACKGROUND OF INVENTION

The present invention relates to a safe and an efficient method for separately recovering a racemic isomer and a meso isomer of azo compounds showing activity at low temperature from an isomeric mixture of the racemic isomer and the meso isomer.

In a field of polymer compounds, study has recently been conducted on increase of polymerization speed in order to improve polymerization degree.

On the other hand, azo compounds showing activity at low temperature, which have been useful polymerization initiators, exist as an isomeric mixture of a racemic isomer and a meso isomer and usually use has been made of the mixture as it is, but it has been known that a racemic isomer has high solubility in organic solvents as compared with a meso isomer.

Therefore, if a racemic isomer is separately recovered from an isomeric mixture of this kind of azo compound and the racemic isomer is used as a polymerization initiator, a concentration of the polymerization initiator in a reaction solvent could be increased because the racemic isomer has high solubility in organic solvents and thus a polymerization speed can be increased.

Further, the above azo compound has been useful as an initiator for radical reactions and it can specifically proceed a radical addition reaction at room temperature, and thus it could be utilized as an initiator in a field wherein a radical reaction is to be applied in place of a photo reaction. A racemic isomer has been known as preferable also for this purpose, and this has been considered to be caused by difference in a stereo structure such as isomerization of the trans-cis isomer of the azo compound, though details have not yet been clarified.

For instance, when bromomalononitrile ($BrCH(CN)_2$) and 2,3-dimethyl-2-butene are subjected to a radical addition reaction with the use of a racemic isomer of the above azo compound as an initiator of the radical reaction, the object addition product is obtained at a yield of 95%, while use of a meso isomer as an initiator of the radical reaction under the same conditions gives the object addition product only at a yield of 7%.

Thus, effective separation of a racemic isomer and a meso isomer from an isomeric mixture of a racemic isomer and a meso isomer of an azo compound showing activity at low temperature and use of only the separated racemic isomer as a polymerization initiator or an initiator for radical addition reactions have now strongly been demanded.

As methods for separation of a racemic isomer from an isomeric mixture of a racemic isomer and a meso isomer of the azo compound, there has been known a method comprising extracting a racemic isomer from an isomeric mixture of the azo compound with an ether utilizing higher solubility of a racemic isomer of azo compounds showing activity at low temperature in organic solvents as compared with a meso isomer, removing a remaining meso isomer by filtration and removing ether under concentration from a filtrate wherein a racemic isomer is dissolved, whereby the object racemic isomer is obtained (Chim.Ind. (Milan) 1970, 52(11), 1116–20(Ital)), etc.

However, this method is accompanied with such drawbacks that an azo compound showing activity at low temperature which is unstable at room temperature is decomposed because of the heat treatment required and so the use of the azo compound is not preferable in a safe side and there exists risk of fire and explosion because of use of a flammable ether. Therefore, development of a method for separating safely and efficiently the racemic isomer at low temperature without using highly flammable ether has strongly been desired.

SUMMARY OF INVENTION

The present invention has been accomplished under the circumstance as mentioned above and the object is to provide a method for recovering separately a racemic isomer and a meso isomer safely and efficiently from an isomeric mixture of a racemic isomer and a meso isomer of an azo compound showing activity at low temperature.

The present invention relates to a method for separation of a racemic isomer and a meso isomer from an isomeric mixture of a racemic isomer and a meso isomer of a compound shown by the general formula [1]

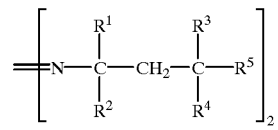

[1]

(wherein $R^1$ and $R^2$ are each independently a lower alkyl group or a cyano group, which are different from each other, $R^3$ and $R^4$ are each independently a lower alkyl group, and $R^5$ is a hydrogen atom or a lower alkoxy group), which comprises treating the mixture with a water soluble organic solvent.

Further, the present invention relates to a method for recovering a racemic isomer of a compound shown by the general formula [1]

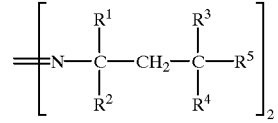

[1]

(wherein $R^1$ and $R^2$ are each independently a lower alkyl group or a cyano group, which are different from each other, $R^3$ and $R^4$ are each independently a lower alkyl group, and $R^5$ is a hydrogen atom or a lower alkoxy group), which comprises treating a mixture of a racemic isomer and a meso isomer of the compound shown by the above general formula [1] with a water soluble organic solvent.

Still further, the present invention relates to a polymerization initiator comprising a racemic isomer of the compound shown by the general formula [1].

Further, the present invention relates to a method for polymerizing a polymerizable monomer, which comprises using, as a polymerization initiator, a racemic isomer of the compound shown by the general formula [1].

Namely, the present inventors have extensively conducted study for realizing the above object to arrive at the finding that the said racemic isomer and the meso isomer can safely and efficiently be separated from each other by subjecting an isomeric mixture of a racemic isomer and a meso isomer of the azo compound, which has activity at low temperature and is unstable at room temperature, shown by the general formula [1] to a treatment with a water soluble organic solvent, and the present invention has been completed on the basis of this finding.

PREFERRED EMBODIMENTS OF INVENTION

In the general formula [1], the lower alkyl group shown by $R^1$ to $R^4$ may be straight chained, branched or cyclic and includes one having generally 1 to 6 carbon atoms, preferably 1 to 3 carbon atoms, which is specifically exemplified by a methyl group, an ethyl group, an n-propyl group, an isopropyl group, an n-butyl group, an isobutyl group, a tert-butyl group, a sec-butyl group, an n-pentyl group, an isopentyl group, a neopentyl group, a tert-pentyl group, a sec-pentyl group, a 2-methylbutyl group, a 1-ethylpropyl group, a cyclopropyl group, a cyclobutyl group, a cyclopentyl group, a cyclohexyl group, etc.

The lower alkoxy group shown by $R^5$ may be straight chained, branched or cyclic and includes one having generally 1 to 6 carbon atoms, preferably 1 to 3 carbon atoms, which is specifically exemplified by a methoxy group, an ethoxy group, an n-propoxy group, an isopropoxy group, an n-butoxy group, an isobutoxy group, a sec-butoxy group, a tert-butoxy group, an n-pentyloxy group, an isopentyloxy group, a sec-pentyloxy group, a tert-pentyloxy group, a neopentyloxy group, an n-hexyloxy group, a cyclopropoxy group, a cyclobutoxy group, a cyclopentyloxy group, a cyclohexyloxy group, etc.

Specific examples of the azo amide compound shown by the general formula [1] are 2,2'-azobis(4-methoxy-2,4-dimethylvaleronitrile) (mfd. by Wako Pure Chemical Industries, LTd.: Trade name V-70) shown by the following formula

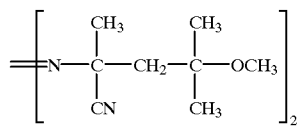

and 2,2'-azobis(2,4-dimethylvaleronitrile) (mfd. by Wako Pure Chemical Industries, Ltd.: Trade name V-65) shown by the following formula

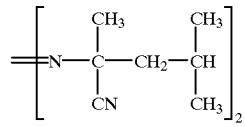

among which 2,2'-azobis (4-methoxy-2,4-dimethylvaleronitrile) is preferable.

The method of the present invention concerning recovering separately the racemic isomer and the meso isomer from a mixture of the racemic isomer and the meso isomer of the azo compound showing activity at low temperature is specifically conducted as follows.

Namely, there is conducted a process step comprising allowing an isomeric mixture of the racemic isomer and the meso isomer of the azo compound showing activity at low temperature which is shown by the general formula [1] to contact with a water soluble organic solvent at low temperature so as to extract the racemic isomer into the water soluble organic solvent. Then, the resulting suspension is filtered and the racemic isomer is crystallized out from the resulting filtrate. On the other hand, the meso isomer is obtained as crystalline remained in the filtration process step. In this way, there can be obtained highly purified racemic and meso isomers, respectively.

The water soluble organic solvent to be used in this method includes preferably one having high solubility against the racemic isomer and low solubility against the meso isomer, which is specifically mentioned by one having solubility of 25 g/dl or higher against the racemic isomer and of 6 g/dl or lower against the meso isomer at about 20° C., preferably one having solubility of 40 g/dl or higher against the racemic isomer and of 1 g/dl or lower against the meso isomer. Those water soluble organic solvents are specifically exemplified by an alcohol such as methanol, ethanol, isopropanol and butanol, a ketone such as acetone and methyl ethyl ketone, acetonitrile, dimethylformamide, dimethylsulfoxide, etc., among which methanol is preferable. The solvent may be used alone or in a suitable combination of two or more thereof.

An amount of the water soluble organic solvent to be used varies depending upon a ratio of the racemic isomer and the meso isomer in the azo compound to be used, an amount of the azo compound, extraction temperature, etc. and is generally 1 to 10 wt parts, preferably 1 to 5 wt parts, relative to 1 wt part of the azo compound used.

When the extraction temperature is too low, solubility of the racemic isomer in the solvent becomes low and extraction effect becomes low, and when it is too high, the racemic isomer dissolved in the solvent is decomposed, and therefore it is generally −10 to 20° C., preferably 5 to 15° C.

Crystallization of the racemic isomer can be conducted after a conventional manner so far used in this kind of field such as a process comprising adding water to a solvent containing the isomer.

An amount of water as a solvent for crystallization is generally 1 to 15 wt parts relative to 1 wt part of a theoretical amount of the racemic isomer to be obtained finally.

After the crystallization of the racemic isomer, the crystal is washed with water, for example, after a process for washing with kneading, to give easily highly purified racemic isomer.

Highly purified object product can also be obtained by a conventional manner such as dehydration, followed by drying under reduced pressure, drying by blowing, etc. after crystallization.

Reaction handlings and after treatments other than the above can be conducted after conventional manners generally conducted in similar reactions.

The racemic isomer of the azo compound showing activity at low temperature obtained by the method of the present invention is easily decomposed by mild heating or photo radiation to generate radicals while nitrogen gas is produced, and therefore, when various kinds of polymerizable monomers exist in the system, the monomers are easily subjected to a polymerization reaction. Further, the said racemic isomer of the azo compound shows high solubility in solvents and therefore concentration of the azo compound in a reaction solvent can be increased, and thus efficiency of the reaction can be increased and it becomes possible to reduce an amount of a solvent during a reaction and to increase an amount of reactants to be supplied in one batch.

Namely, a polymer can be obtained by conducting a polymerization reaction with the use of a polymerizable monomer and the racemic isomer of the azo compound obtained in the present invention as an initiator of a radical reaction in a suitable solvent or in the absence of a solvent, if necessary, under an inert gas stream after a conventional manner.

After treatments after polymerization can be conducted by a conventional manner generally conducted in this kind of technical field.

Upon conducting a polymerization reaction, a chain-transferring agent (such as laurylmercaptan, octylmercaptan, butylmercaptan, 2-mercaptoethanol and butyl thioglycolate), if necessary, may be added to a reaction solution so as to regulate a molecular weight.

The polymerization reaction is conducted by a solution polymerization method, a bulk polymerization method, a suspension polymerization method, an emulsion polymerization method, a dispersion polymerization method or others.

The polymerizable monomer includes α, β-ethylenically unsaturated monomer which is shown, for example, by the general formula [2]

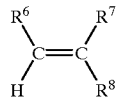

[2]

(wherein $R^6$ is a hydrogen atom, a lower alkyl group, a carboxyl group, a carboxyalkyl group, an alkyloxycarbonyl group, a cyano group or an aldehyde group, $R^7$ is a hydrogen atom, a lower alkyl group, a carboxyl group, an alkyloxycarbonyl group, a cyano group or a halogen atom, $R^8$ is a hydrogen atom, a lower alkyl group, a haloalkyl group, an aryl group which may have a substituent, an aliphatic heterocyclic group, an aromatic heterocyclic group, a halogen atom, an alkyloxycarbonyl group, a cyano group, a cyano-containing alkyl group, an acyloxy group, a carboxyl group, a carboxyalkyl group, an aldehyde group, a carbamoyl group or an N-alkylcarbamoyl group, and $R^6$ and $R^7$ may form an alicyclic ring together with the adjacent —C=C— group).

The lower alkyl group shown by $R^6$ to $R^8$ in the general formula [2] may be straight chained, branched or cyclic and includes those having 1 to 6 carbon atoms, which is specifically exemplified by a methyl group, an ethyl group, an n-propyl group, an isopropyl group, an n-butyl group, an isobutyl group, a tert-butyl group, a sec-butyl group, an n-pentyl group, an isopentyl group, a tert-pentyl group, a 1-methylpentyl group, an n-hexyl group, an isohexyl group, a cyclopropyl group, a cyclopentyl group, a cyclohexyl group, etc.

The carboxyalkyl group shown by $R^6$ and $R^8$ includes those derived by substituting a part of the hydrogen atoms of the lower alkyl groups mentioned above with a carboxyl group, which is specifically exemplified by a carboxymethyl group, a carboxyethyl group, a carboxypropyl group, a carboxybutyl group, a carboxypentyl group, a carboxyhexyl group, etc.

The alkyloxycarbonyl group shown by $R^6$ to $R^8$ includes preferably those having 2 to 11 carbon atoms, which is specifically exemplified by a methoxycarbonyl group, an ethoxycarbonyl group, a propoxycarbonyl group, a butoxycarbonyl group, a pentyloxycarbonyl group, a hexyloxycarbonyl group, a heptyloxycarbonyl group, a 2-ethylhexyloxycarbonyl group, an octyloxycarbonyl group, a nonyloxycarbonyl group, a decyloxycarbonyl group, etc.

The halogen atom shown by $R^7$ and $R^8$ includes a fluorine atom, a chlorine atom, a bromine atom, an iodine atom, etc.

The haloalkyl group shown by $R^8$ includes one having 1 to 6 carbon atoms derived by halogenating (e.g. fluorinating, chlorinating, brominating, iodinating, etc.) the lower alkyl group mentioned above, which is specifically exemplified by a chloromethyl group, a bromomethyl group, a trifluoromethyl group, a 2-chloroethyl group, a 3-chloropropyl group, a 3-bromopropyl group, a 3,3,3-trifuluoropropyl group, a 4-chlorobutyl group, a 5-chloropentyl group, a 6-chlorohexyl group, etc.

The aryl group in the aryl group which may have a substituent shown by $R^8$ includes a phenyl group, a tolyl group, a xylyl group, a naphthyl group, and the substituent includes a lower alkoxy group, and the specific examples thereof are a methoxyphenyl group, a tert-butoxyphenyl group, etc.

The aliphatic heterocyclic group shown by $R^8$ includes preferably 5- or 6-membered one containing 1 to 3 hetero atoms such as a nitrogen atom, an oxygen atom and a sulfur atom, and the specific examples are a pyrrolidyl-2-on group, a piperidyl group, a piperidino group, a piperazinyl group, a morpholino group, etc.

The aromatic heterocyclic group shown by $R^8$ includes 5- or 6-membered one containing 1 to 3 hetero atoms such as a nitrogen atom, an oxygen atom and a sulfur atom, and the specific examples are a pyridyl group, an imidazolyl group, a thiazolyl group, a furanyl group and a pyranyl group.

The cyano-containing alkyl group shown by $R^8$ includes one derived by substituting a part of the hydrogen atoms of the lower alkyl groups mentioned above with a cyano group, which is specifically exemplified by a cyanomethyl group, a 2-cyanoethyl group, a 2-cyanopropyl group, a 3-cyanopropyl group, a 2-cyanobutyl group, a 4-cyanobutyl group, a 5-cyanopentyl group, a 6-cyanohexyl group, etc.

The acyloxy group shown by $R^8$ includes one having 2 to 20 carbon atoms derived from a carboxylic acid, which is specifically exemplified by an acetyloxy group, a propionyloxy group, a butylyloxy group, a pentanoyloxy group, a hexanoyloxy group, a heptanoyloxy group, an octanoyloxy group, a nonanoyloxy group, a decanoyloxy group, a benzoyloxy group, etc.

The N-alkylcarbamoyloxy group shown by $R^8$ includes one derived by substituting a part of the hydrogen atoms of carbamoyl group with an alkyl group, which is specifically exemplified by an N-methylcarbamoyl group, an N-ethylcarbamoyl group, an N-n-propylcarbamoyl group, an N-isopropylcarbamoyl group, an N-n-butylcarbamoyl group, an N-t-butylcarbamoyl group, etc.

The case where $R^6$ and $R^7$ are bound together with the adjacent —C=C— group to form alicyclic ring includes one where an unsaturated alicyclic ring having 5 to 10 carbon atoms is formed, and the specific examples of those groups are a norbornene ring, a cyclopentene ring, a cyclohexene ring, a cyclooctene ring, a cyclodecene ring, etc.

The specific examples of the α, β-ethylenically unsaturated monomer includes an ethylenically unsaturated aliphatic hydrocarbon having 2 to 20 carbon atoms such as ethylene, propylene, butylene and isobutylene, an ethylenically unsaturated aromatic hydrocarbon having 8 to 20 carbon atoms such as styrene, 4-methylstyrene, 4-ethylstyrene and divinylbenzene, an alkenyl ester having 3 to 20 carbon atoms such as vinyl formate, vinyl acetate, vinyl propionate and isopropenyl acetate, a halogen-containing ethylenically unsaturated compound such as vinyl chloride, vinylidene chloride, vinylidene fluoride and tetrafluoroethylene, an ethylenically unsaturated carboxylic acid (it may form an alkaline metal salt such as sodium salt and potassium salt, an ammonium salt, etc) having 3 to 20 carbon atoms such as acrylic acid, methacrylic acid, itaconic acid, maleic acid, fumaric acid, crotonic acid, vinyl acetic acid, allyl acetic acid and vinyl benzoic acid, an ethylenically unsaturated carboxylic acid ester such as methyl methacrylate, ethyl methacrylate, propyl methacrylate, butyl methacrylate, 2-ethylhexyl methacrylate, lauryl methacrylate, stearyl methacrylate, methyl acrylate, ethyl acrylate, butyl acrylate, 2-ethylhexyl acrylate, methyl itaconate, ethyl itaconate, methyl maleate, ethyl maleate, methyl fumarate, ethyl fumarate, methyl crotonate, ethyl crotonate and methyl 3-butenoate, a cyano-containing ethylenically unsaturated compound having 3 to 20 carbon atoms such as acrylonitrile, methacrylonitrile and allyl cyanide, an ethylenically unsaturated amide compound having 3 to 20 carbon atoms such as acrylamide and methacrylamide, an ethylenically unsaturated aldehyde having 3 to 20 carbon atoms such as acrolein and croton aldehyde, an ethylenically unsaturated aliphatic heterocyclic amine having 5 to 20 carbon atoms such as N-vinylpyrrolidone and vinylpiperidine, an ethylenically unsaturated aromatic heterocyclic amine having 5 to 20 carbon atoms such as vinylpyridine and 1-vinylimidazole, etc.

Those monomer may be used alone or in a suitable combination of two or more thereof.

The solvent includes an ether such as tetrahyrofuran, diethyl ether and dioxane, a halogenated hydrocarbon such as chloroform, methylene chloride and 1,2-dichloroethane, a hydrocarbon such as n-hexane, petroleum ether, toluene, benzene and xylene, an alcohol such as methanol, ethanol and isopropanol, a ketone such as acetone, methyl ethyl ketone and methylisobutyl ketone, acetonitrile, N,N-dimethylformamide, dimethylsulfoxide, etc. The solvent may be used alone or in a suitable combination of two or more thereof.

The inert gas includes nitrogen gas, argon gas, etc.

Upon the above polymerization reaction, an amount of the racemic isomer of the azo compound obtained in the method of the present invention varies depending upon the kind of the polymerizable monomer to be used, and it is generally 0.01 to 100 wt %, preferably 0.05 to 50 wt % relative to the monomer.

The reaction temperature is generally 30 to 130° C., preferably 40 to 120° C., more preferably 50 to 90° C.

The reaction time varies depending upon the reaction temperature, the kind of the polymerizable monomer, the kind of the azo compound of the present invention and other conditions and it is generally 2 to 24 hours.

Reaction handlings and after treatments other than the above can be conducted after a conventional manner applied in similar reactions.

As mentioned above, the present invention requires no heating treatment which is necessary for concentration of a solvent as in known methods and no use of flammable ether, and thus the present invention has such an advantage as the racemic and meso isomers being capable of obtaining safely and at high yield.

Further, the method of the present invention is conducted by extraction and crystallization, and thus the racemic and meso isomers can be obtained as highly purified crystalline.

In the following, the present invention is explained in details with referring to Examples, and the present invention is not limited thereto by any means.

EXAMPLES

Example 1

To 280 ml of methanol kept at 10° C. was poured 108.1 g of 2,2'-azobis (4-methoxy-2,4-dimethylvaleronitrile (mfd. by Wako Pure Chemical Industries, Ltd.: Trade Name V-70, meso isomer:racemic isomer=54.0:46.0 by NMR analysis, m.p. 58.9–87.9° C., loss on drying of 7.5 %) with stirring, and the resulting suspension was stirred at 5° C. for 30 minutes. The remaining crystal (meso isomer) was recovered by filtration and washed with 50 ml of methanol to give 54.2 g of meso isomer (yield 97.7%, purity 97.3%, m.p. 92.4 to 96.5° C.).

Then, 495 ml of water was poured into the filtrate under keeping at −7° C., followed by stirring for 1 hour to crystallize a racemic isomer. The resulting crystal was recovered by filtration and washed with 75 ml of water, followed by drying to give 43.3 g of a racemic isomer (yield 91.7%, purity 97.4%, m.p. 58.6 to 60.1° C.).

Example 2

To 150 ml of methanol kept at 20° C. was poured 108.1 g of 2,2'-azobis (4-methoxy-2,4-dimethylvaleronitrile (mfd. by Wako Pure Chemical Industries, Ltd.: Trade Name V-70, meso isomer:racemic isomer=54.0:46.0 by NMR analysis, m.p. 58.9–87.9° C., loss on drying of 7.5%) with stirring, and the resulting suspension was stirred at 20° C. for 30 minutes. The remaining crystal (meso isomer) was recovered by filtration and dried to give 54.7 g of meso isomer (yield 95.5%, purity 94.3%).

Then, 150 ml of water was poured into the filtrate under keeping at 0° C., followed by stirring for 1 hour to crystallize a racemic isomer. The resulting crystal was recovered by filtration and washed with 75 ml of water, followed by drying to give 41.6 g of a racemic isomer (yield 87.7%, purity 97.0%).

Example 3

To 200 ml of methanol kept at 15° C. was poured 108.1 g of 2,2'-azobis (4-methoxy-2,4-dimethylvaleronitrile (mfd. by Wako Pure Chemical Industries, Ltd.: Trade Name V-70, meso isomer:racemic isomer=54.0:46.0 by NMR analysis, m.p. 58.9–87.9° C., loss on drying of 7.5%) with stirring, and the resulting suspension was stirred at 15° C. for 30 minutes.

Then same treatment as in Example 2 except for an amount of water to add to the filtrate being 200 ml was conducted to give the object meso isomer and racemic isomer.
Meso isomer: 55.9 g (yield 98.0%, purity 94.7%)
Racemic isomer: 40.9 g (yield 86.4%, purity 97.2%)

Example 4

To 450 ml of methanol kept at 5° C. was poured 108.1 g of 2,2'-azobis (4-methoxy-2,4-dimethylvaleronitrile (mfd. by Wako Pure Chemical Industries, Ltd.: Trade Name V-70, meso isomer:racemic isomer=54.0:46.0 by NMR analysis, m.p. 58.9–87.9° C., loss on drying of 7.5%) with stirring, and the resulting suspension was stirred at 5° C. for 30 minutes.

Then same treatment as in Example 2 except for an amount of water to add to the filtrate being 450 ml was conducted to give the object meso isomer and racemic isomer.
Meso isomer: 55.3 g (yield 98.5%, purity 96.2%)
Racemic isomer: 39.5 g (yield 83.3%, purity 97.0%)

Example 5

To 778 ml of methanol kept at 0° C. was poured 108.1g of 2,2'-azobis (4-methoxy-2,4-dimethylvaleronitrile (mfd. by Wako Pure Chemical Industries, Ltd.: Trade Name V-70, meso isomer:racemic isomer=54.0:46,0 by NMR analysis, m.p. 58.9–87.9° C., loss on drying of 7.5%) with stirring, and the resulting suspension was stirred at 0° C. for 30 minutes.

Then same treatment as in Example 2 except for an amount of water to add to the filtrate being 778 ml was conducted to give the object meso isomer and racemic isomer.

Meso isomer: 54.0 g (yield 97.4%, purity 97.4%)
Racemic isomer: 36.7 g (yield 77.7%, purity 97.4%)

Example 6

To 10 ml of dimethylsulfoxide was added 2.0 g (37.6 mmol) of acrylonitrile and 0.136 g (0.44 mmol) of the racemic isomer of 2,2'-azobis (4-methoxy-2,4- dimethylvaleronitrile (V-70) obtained in Example 1 as an initiator. Then, the dimethylsulfoxide solution was added to a polymerization tube, which was made of a glass tube (Pyrexglass: a trade name of Coming, Inc.), followed by substituting the air in the tube for nitrogen gas and then removing oxygen from the solution under reduced pressure, followed by sealing the tube under melting. After sealing the tube, a polymerization reaction was conducted at 45° C., during a polymerization, the reaction solution was sampled at predetermined time, and the reaction solution was poured into 150ml of methanol, followed by crystallizing to precipitate the polymer product, respectively.

A polymerization rate of the obtained polymer was calculated by the following equation.

Polymerization rate(%)=(obtained polymer(g))÷(initial acrylonitrile(g))×100

The results obtained are shown in Table 1.

TABLE 1

| A polymerization time | 1H | 2H | 3H | 4H |
|---|---|---|---|---|
| A polymerization rate (%) | 46 | 68 | 85 | 90 |

EFFECT OF INVENTION

The present invention is to provide a method for separating safely and easily a racemic isomer and a meso isomer from an isomeric mixture of an azo compound showing activity at low temperature, and according to the method of the present invention, use of highly flammable ether as a solvent as in known methods is not required any more and further removal of an extraction solvent by heating is not required, and therefore the racemic and meso isomers in highly purified form can be prepared remarkably safely and at high yield.

What is claimed:

1. A method for separation of a racemic isomer and a meso isomer from a mixture of a racemic isomer and a meso isomer of a compound shown by the general formula

[1]

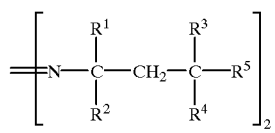

(wherein $R^1$ and $R^2$ are each independently a lower alkyl group or a cyano group, which are different from each other, $R^3$ and $R^4$ are each independently a lower alkyl group, and $R^5$ is a hydrogen atom or a lower alkoxy group), which comprises treating the mixture with a water soluble organic solvent.

2. A method according to claim 1, wherein in the general formula [1] $R^1$ and $R^2$ is each independently an alkyl group having 1 to 6 carbon atoms or a cyano group, $R^3$ and $R^4$ are each independently an alkyl group having 1 to 6 carbon atoms, and $R^5$ is a hydrogen atom or an alkoxy group having 1 to 6 carbon atoms.

3. A method according to claim 1, wherein in the general formula [1] $R^1$ and $R^2$ is each independently a methyl group, an ethyl group or a cyano group, $R^3$ and $R^4$ are each independently a methyl group or an ethyl group, and $R^5$ is a hydrogen atom, a methoxy group or an ethoxy group.

4. A method according to claim 1, wherein in the general formula [1] any one of $R^1$ and $R^2$ is a methyl group and the other is a cyano group, $R^3$ and $R^4$ are a methyl group and $R^5$ is a methoxy group.

5. A method according to claim 1, wherein the treatment with a water soluble organic solvent is an extraction treatment.

6. A method according to claim 1, wherein the treatment with a water soluble organic solvent is conducted at 20° C. or lower.

7. A method according to claim 1, wherein the treatment with a water soluble organic solvent is conducted at −10 to 20° C.

8. A method according to claim 1, wherein the water soluble organic solvent is one having solubility of 25 g/dl or higher against the racemic isomer and of 6 g/dl or lower against the meso isomer.

9. A method according to claim 1, wherein the water soluble organic solvent is an alcohol, a ketone, acetonitrile, dimethylformamide or dimethylsulfoxide.

10. A method according to claim 1, wherein the water soluble organic solvent is methanol.

11. A method for recovering a racemic isomer of a compound shown by the general formula [1]

[1]

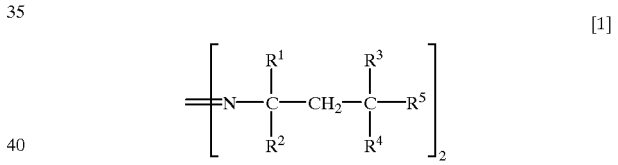

(wherein $R^1$ and $R^2$ are each independently a lower alkyl group or a cyano group, which are different from each other, $R^3$ and $R^4$ are each independently a lower alkyl group, and $R^5$ is a hydrogen atom or a lower alkoxy group), which comprises treating a mixture of a racemic isomer and a meso isomer of the compound shown by the above general formula [1] with a water soluble organic solvent.

12. A method according to claim 11, wherein in the general formula [1] $R^1$ and $R^2$ is each independently an alkyl group having 1 to 6 carbon atoms or a cyano group, $R^3$ and $R^4$ are each independently an alkyl group having 1 to 6 carbon atoms, and $R^5$ is a hydrogen atom or an alkoxy group having 1 to 6 carbon atoms.

13. A method according to claim 11, wherein in the general formula [1] $R^1$ and $R^2$ is each independently a methyl group, an ethyl group or a cyano group, $R^3$ and $R^4$ are each independently a methyl group or an ethyl group, and $R^5$ is a hydrogen atom, a methoxy group or an ethoxy group.

14. A method according to claim 11, wherein in the general formula [1] any one of $R^1$ and $R^2$ is a methyl group and the other is a cyano group, $R^3$ and $R^4$ are a methyl group and $R^5$ is a methoxy group.

15. A method according to claim 11, wherein the treatment with a water soluble organic solvent is an extraction treatment.

16. A method according to claim 11, wherein the treatment with a water soluble organic solvent is conducted at 20° C. or lower.

17. A method according to claim 11, wherein the treatment with a water soluble organic solvent is conducted at −10 to 20° C.

18. A method according to claim 11, wherein the water soluble organic solvent is one having solubility of 25 g/dl or higher against the racemic isomer and of 6 g/dl or lower against the meso isomer.

19. A method according to claim 11, wherein the water soluble organic solvent is an alcohol, a ketone, acetonitrile, dimethylformamide or dimethylsulfoxide.

20. A method according to claim 11, wherein the water soluble organic solvent is methanol.

21. A polymerization initiator, which comprises a racemic isomer of 2,2'-azobis(4-methoxy-2,4-dimethylvaleronitrile).

22. A method for polymerizing a polymerizable monomer, which comprises using, as a polymerization initiator, a racemic isomer of 2,2'-azobis (4-methoxy-2,4-dimethylvaleronitrile).

23. A polymerization initiator, which comprises a racemic isomer of 2,2'-azobis(4-methoxy-2,4-dimethylvaleronitrile) recovered by the method of claim 1.

* * * * *